(12) United States Patent
Reyland et al.

(10) Patent No.: US 10,076,520 B2
(45) Date of Patent: Sep. 18, 2018

(54) USE OF TYROSINE KINASE INHIBITOR IN CANCER TREATMENT

(71) Applicant: THE REGENTS OF THE UNIVERSITY OF COLORADO, A BODY CORPORATE, Denver, CO (US)

(72) Inventors: Mary E. Reyland, Denver, CO (US); Sten Wie, Denver, CO (US); James DeGregori, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 15/029,617

(22) PCT Filed: Oct. 17, 2014

(86) PCT No.: PCT/US2014/061038
§ 371 (c)(1),
(2) Date: Apr. 14, 2016

(87) PCT Pub. No.: WO2015/058034
PCT Pub. Date: Apr. 23, 2015

(65) Prior Publication Data
US 2016/0228436 A1    Aug. 11, 2016

Related U.S. Application Data

(60) Provisional application No. 61/893,132, filed on Oct. 18, 2013.

(51) Int. Cl.
*A61K 31/506* (2006.01)
*A61K 31/5025* (2006.01)
*A61K 31/517* (2006.01)
*A61K 45/06* (2006.01)
*A61K 31/496* (2006.01)

(52) U.S. Cl.
CPC .......... *A61K 31/506* (2013.01); *A61K 31/496* (2013.01); *A61K 31/5025* (2013.01); *A61K 31/517* (2013.01); *A61K 45/06* (2013.01)

(58) Field of Classification Search
USPC .................. 514/8.1, 9.1, 19.3, 19.8, 248
See application file for complete search history.

(56) References Cited

U.S. PATENT DOCUMENTS

2012/0295917 A1* 11/2012 Kim ..................... C07D 401/04
514/252.18

OTHER PUBLICATIONS

Riely (Journal of Clinical Oncology; vol. 27, No. 2, 264-270, Jan. 10, 2009).*
Arora (The Journal of Pharmacology and Experimental Therapeutics; 315(3), 971-979, 2005).*
Boehrer (cell Cycle; 10:18, 3168-3175; Sep. 15, 2011).*

* cited by examiner

*Primary Examiner* — Pancham Bakshi
(74) *Attorney, Agent, or Firm* — Sheridan Ross P.C.

(57) ABSTRACT

The present invention provides methods for reducing apoptosis of non-cancerous cells during a cancer treatment and beneficial effects associated with reducing such apoptosis. In particular, methods of the invention comprise administering a tyrosine kinase inhibitor to a cancer patient who is undergoing cancer treatment in order to reduce apoptosis of non-cancerous cells.

9 Claims, 5 Drawing Sheets

USE OF TYROSINE KINASE INHIBITOR IN CANCER TREATMENT

CROSS-REFERENCE TO RELATED APPLICATIONS

This application claims the priority benefit of U.S. Provisional Application No. 61/893,132, filed Oct. 18, 2013, which is incorporated herein by reference in its entirety.

STATEMENT REGARDING FEDERALLY FUNDED RESEARCH

This invention was made with government support under grant number DE015648 awarded by the National Institutes of Health. The government has certain rights in the invention.

FIELD OF THE INVENTION

The present invention relates to reducing apoptosis of non-cancerous cells during a cancer treatment. In particular, the present invention relates to administering a tyrosine kinase inhibitor to a cancer patient undergoing a cancer treatment in order to reduce apoptosis of non-cancerous cells.

BACKGROUND OF THE INVENTION

Cancer is one of the leading causes of death. However, with the early detection and treatment, many cancer patients can live a long productive life. Unfortunately, cancer treatment can be extremely painful or discomforting to cancer patients. Some cancer patients even stop cancer treatment due to extreme pain and/or discomfort during treatment.

Cancer treatment typically involves a relatively indiscriminate killing of both cancerous cells and non-cancerous, e.g., normal, cells. Many side-effects of cancer treatment can be attributed to killing of non-cancerous cells during cancer treatment. It is believed that many, if not all, of the undesirable side-effects of cancer treatment are in large part due to apoptosis of non-cancerous cells due to cancer treatment.

While some cancer treatments have been developed that target mainly the cancerous cells, such treatments are not widely available, are often time consuming, or require additional laboratory work.

Therefore, there is a need for a general method for reducing apoptosis of non-cancerous cells during cancer treatment to reduce the side-effects of cancer treatment due to apoptosis of non-cancerous cells during such a treatment.

SUMMARY OF THE INVENTION

Some aspects of the invention provide a method for reducing apoptosis of non-cancerous cells during a cancer treatment, said method comprising administering a therapeutically effective amount of a tyrosine kinase inhibitor prior to administering a cancer treatment to a cancer patient.

Another aspects of the invention provide a method for treating a cancer patient, said method comprising administering a tyrosine kinase inhibitor to a cancer patient prior to administering a cancer treatment to protect noncancerous cells from said cancer treatment, wherein administration of said tyrosine kinase inhibitor significantly reduces the amount of apoptosis of noncancerous cells.

Yet other aspects of the invention provide a method for reducing a side-effect of a cancer treatment in a cancer patient, said method comprising administering a tyrosine kinase inhibitor to said cancer patient prior to administering a cancer treatment to said patient.

DETAILED DESCRIPTION OF THE INVENTION

Figure 1:
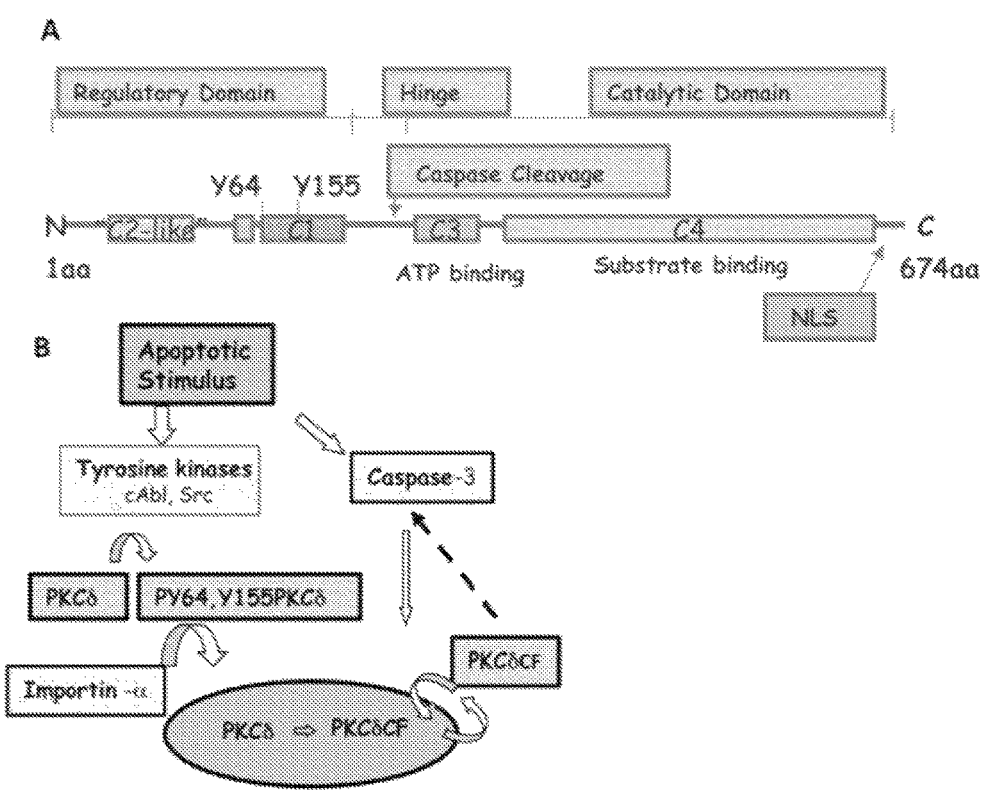
FIG. 1 is a schematic illustration showing role of tyrosine phosphorylation of PKCδ in apoptosis. Panel A shows structure of PKCδ showing positions of Y64, Y155, caspase cleavage and the NLS. Panel B shows a schematic illustration of current model of PKCδ and salivary acinar cell apoptosis.

The isoforms of the protein kinase C ("PKC") family are activated in response to various stimuli (e.g., mitogenic stimuli, to inflammatory stimuli, and to stress) and play important roles in a variety of cellular functions including apoptosis. In particular, PKCδ a member of the novel PKC subfamily, is actively involved in cell apoptosis in a stimulus and tissue specific manner. It is believed that PKCδ both regulates the expression and function of apoptosis related proteins and is itself a target for caspases. In addition, it is believed phosphorylation of PKCδ on distinct tyrosine residues and its association with specific apoptotic related proteins such as c-Abl, DNA-PK, p73 and lamin B are pivotal to its function in cell apoptosis. In particular, as shown in FIG. 1, it is believed tyrosine phosphorylation and importin-α binding are key regulatory steps in apoptosis as they control nuclear import. Moreover, caspase (in particular caspase 3) cleavage of PKCδ is thought to amplify the apoptotic response.

Referring again to FIG. 1, it is believed that activation of c-Abl- or Src-family of kinases stimulates apoptosis. While apoptosis can be a part of natural process, in cancer treatment apoptosis of non-cancerous cells have been shown to be one of the main causes of cancer treatment side-effects. Thus, it is believed that by reducing apoptosis of non-cancerous cells one can significantly reduce the side-effects of cancer treatment. As used herein, the term "cancer treatment" includes radiotherapy and chemotherapy to treat cancer.

Some aspects of the invention provide a method for reducing apoptosis of non-cancerous cells during a cancer treatment. Typically, the method comprises administering a therapeutically effective amount of a tyrosine kinase inhibitor ("TKI") prior to administering a cancer treatment to a cancer patient. As used herein, the term "reducing apoptosis of non-cancerous cells" refers to reducing at least 30%, typically at least 60%, and often at least 80% of non-cancerous cell apoptosis using the method of the invention relative to cancer treatment that does not include administration of a TKI prior to cancer treatment. Typically, the TKI is administered at least 30 min, typically at least 45 min, and often at least 60 min prior to administering cancer treatment to a cancer patient.

In some embodiments, the method further comprises administering a second TKI after administering said cancer treatment to said cancer patient. The second TKI can be the same as the TKI that is administered prior to cancer treatment or it can be a different TKI. Typically, the same TKI is used pre- and post-cancer treatment. When a TKI is administered after cancer treatment, typically it is administered within 60 min, often within 120 min, and most often within 180 min after cancer treatment.

Still in other embodiments, said steps of administering said tyrosine kinase inhibitor prior to said cancer treatment reduces apoptosis of non-cancerous cells by at least 30%, typically by at least 60%, and often by at least 80%.

Yet in other embodiments, said cancer treatment consists of radiotherapy. In other embodiments, said cancer treatment consists of chemotherapy.

Still in other embodiments, said cancer treatment consists of combination of radiotherapy and chemotherapy. In such embodiments, said TKI can also be administered between chemotherapy and radiotherapy sessions.

Typically, said tyrosine kinase inhibitor inhibits c-Abl and/or Src-family kinases.

Exemplary tyrosine kinase inhibitors that are useful in methods of the invention include, but are not limited to, dasatinib, imatinib, ponatinib, saracatinib, lapatinb, gefitinib, sorafenib, erlotinib, sunitinib, nilotinib, vandetanib, bosutinib, afatinib and regorafenib.

Generally, methods of the invention can be used in preventing apoptosis of non-cancerous cells in cancer treatment for any type of cancer. Exemplary cancers for which methods of the invention is useful include, but are not limited to, head and neck cancer, pancreatic cancer, stomach cancer, breast cancer, colon cancer, lung cancer, liver cancer, leukemia, bone cancer, ovarian cancer, cervical cancer, brain cancer, skin cancer, prostate cancer, thyroid cancer, etc.

Other aspects of the invention include methods for treating a cancer patient. Such methods include administering a tyrosine kinase inhibitor to a cancer patient prior to administering a cancer treatment to protect non-cancerous cells from said cancer treatment, wherein administration of said tyrosine kinase inhibitor significantly reduces the amount of apoptosis of non-cancerous cells. Typically, the tyrosine kinase is administered to the cancer patient prior to administering cancer treatment. In some cases, the tyrosine kinase inhibitor can also be administered post cancer treatment as discussed above.

Yet other aspects of the invention include methods for reducing a side-effect of a cancer treatment in a cancer patient. Such methods include administering a therapeutically effective amount of tyrosine kinase inhibitor to said cancer patient prior to administering a cancer treatment. As used herein, the term "therapeutically effective amount" means the amount of a TKI that, when administered to a cancer patient, is sufficient to reduce apoptosis of non-cancerous cells. The "therapeutically effective amount" will vary depending on the TKI, the severity of cancer treatment and the age, weight, etc., of the cancer patient.

As shown in the Examples section, the present inventors have discovered that tyrosine kinase inhibitors inhibit irradiation-induced and chemotherapy-induced (e.g., etoposide-induced) apoptosis of cells in vivo as well as cultured rat salivary acinar cells (cell line ParC5). These inhibitors block tyrosine phosphorylation of PKCδ and its import into the nucleus. Without being bound by any theory, since nuclear import of PKCδ is required for apoptosis, this is believed to be at least one of the mechanisms of action by which TKIs inhibit apoptosis of non-cancerous cells. Based on the magnitude of apoptosis inhibition (e.g., >80% in some instances), additional targets or mechanisms are believed to be likely.

Typically, the TKI is administered in formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. In some embodiments, the TKI is administered by direct injection at or near the site of radio- or chemo-therapy.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

Figure 2:
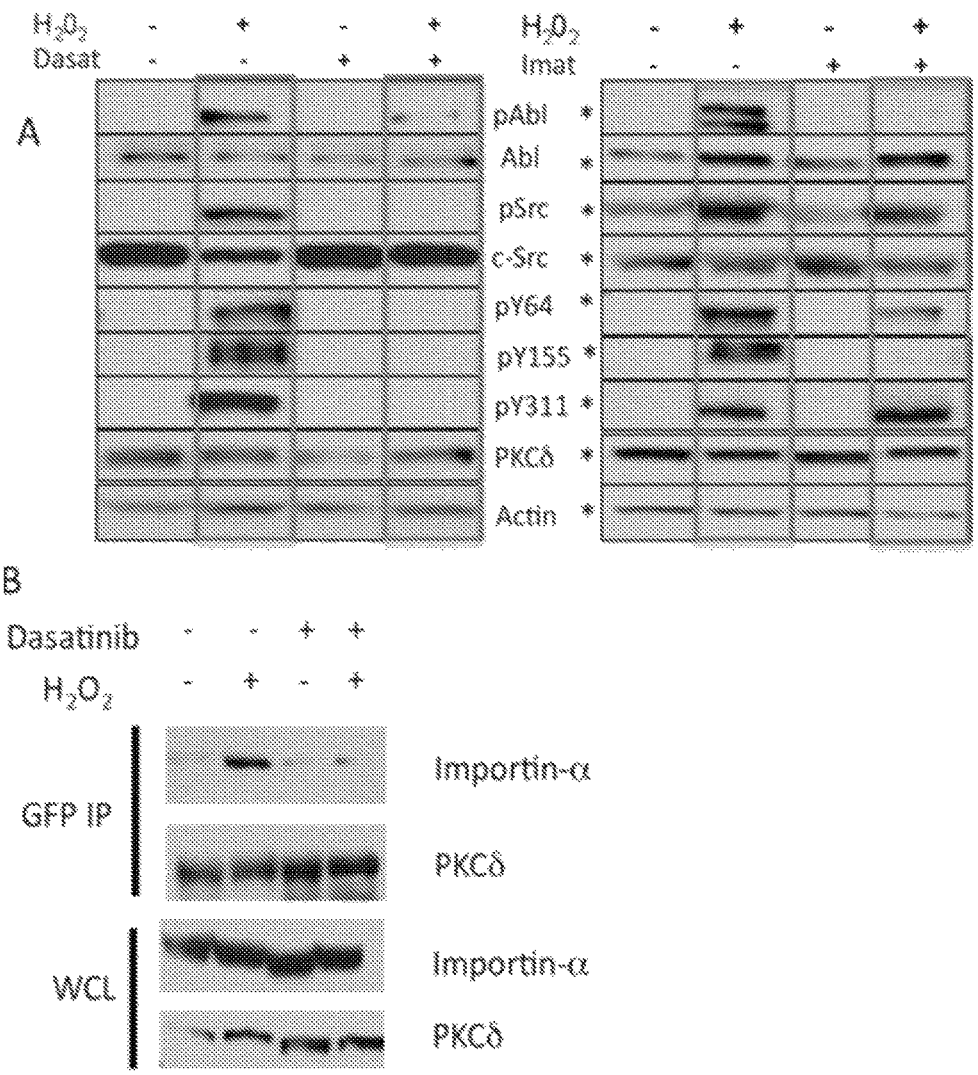
FIG. 2 shows results of treating cells with tyrosine kinase inhibitors, i.e., TKIs, (e.g., dasatinib and imatinib) prior to exposing the cells to a cytotoxic agent hydrogen peroxide. As can be seen in panel A, dasatinib suppresses phosphorylation of PKCδ at Y155, Y64 and Y311 in cells treated with $H_2O_2$. Panel A also shows imatinib suppresses phosphorylation of PKCδ at Y155 in cells treated with $H_2O_2$. As seen in Panel B, both drugs block importin-α binding (data not shown for imatinib).

ParC5 cells were pre-treated with dasatinib or imatinib for 30 mins prior to addition of hydrogen peroxide to induce apoptosis. Cell lysates were probed by immunoblot as indicated. Hydrogen peroxide induced phosphorylation of PKCδ at tyrosine 64 (Y64), tyrosine 155 (Y155) and tyrosine 311 (Y311). Pretreatment of cells with dasatinib (Panel A of FIG. 2, left) inhibited phosphorylation of PKCδ at all sites, consistent with inhibition of both c-Src and c-Abl activation as assayed using antibodies to pY412Abl and pY416Src. Pane A of FIG. 2, right, shows a similar experiment in which ParC5 cells were pre-treated with imatinib. In this experiment imatinib inhibited phosphorylation of PKCδ at Y155 only.

293T cells were transfected with pGFP-PKCδ. Transfected cells were left untreated, or pre-treated with dasatinib prior to treatment with hydrogen peroxide. Lysates were incubated with an anti-GFP to immunoprecipitate GFPPKCδ and immunobloted for importin-α. The results are shown in panel B of FIG. 2. While importin-α immunoprecipitated with PKCδ in cells treated with hydrogen peroxide, this interaction did not occur in cells pre-treated with dasatinib. Similar results were seen when cells were pretreated with imatinib (data not shown)

Example 2

Figure 3A:
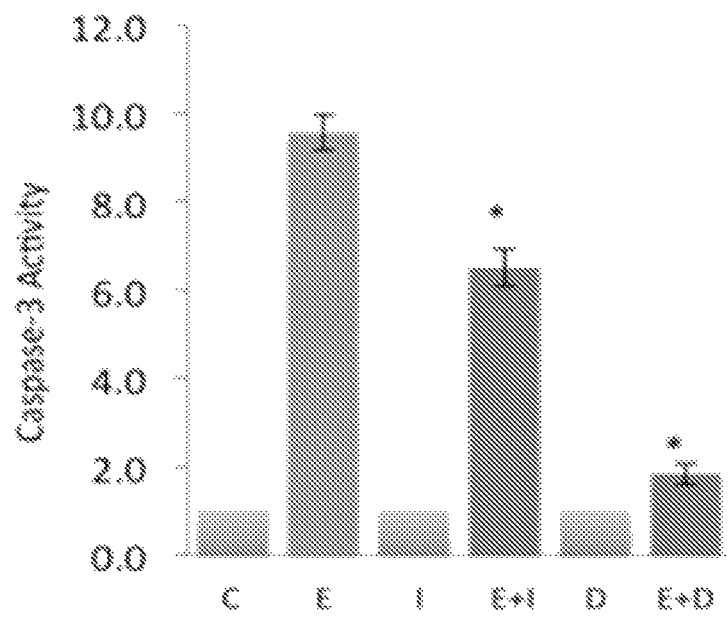
FIG. 3A shows the results of ParC5 cells that were treated with DMSO (C), Imatinib (I), Dasatinib (D), 50 μM of etoposide (E), or the combination of etoposide and inhibitors as indicated prior to irradiation.

ParC5 cells were treated with DMSO (control), imatinib, dasatinib, or 50 μM of etoposide or the combination of etoposide and tyrosine kinase inhibitors (TKIs). TKIs were added to cells 30 mins prior to addition of etoposide. Relative caspase-3 activity for each was measured, which is indicative of apoptosis. As shown in FIG. 3A, imatinib and dasatinib both significantly reduced apoptosis.

Figure 3B:
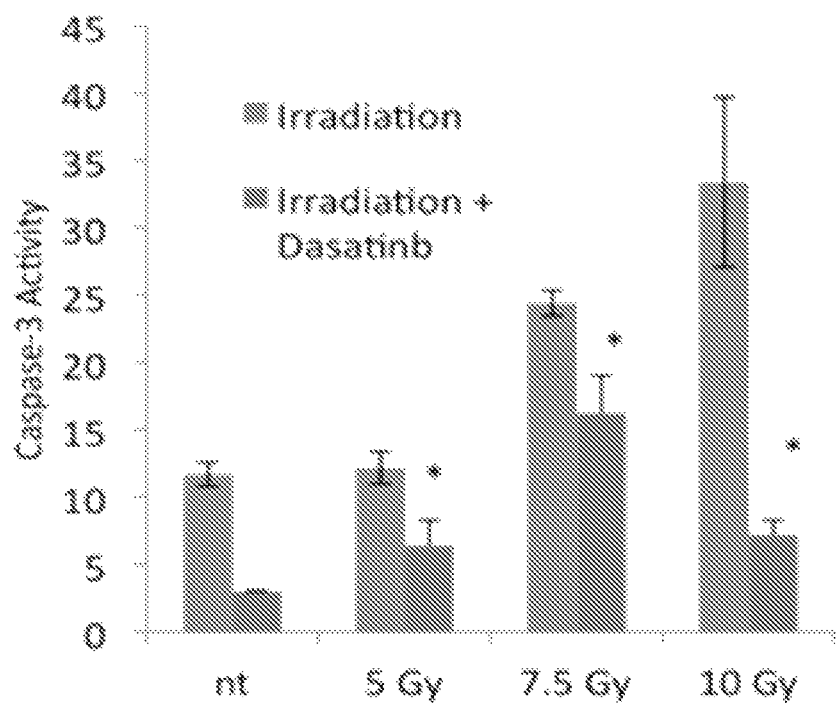
FIG. 3B shows the relative caspase-3 activity of ParC5 cells after irradiation at various radiation levels. Left bars are caspace-3 activity of cells that were left untreated and the right bars are caspase-3 activity of cells that were pre-treated with Dasatinib (20 nM) prior to irradiation.

ParC5 cells were left untreated or pre-treated with 20 nM of dasatinib 30 mins prior to irradiation (5, 7.5 or 10 Gy). Relative caspase-3 activity was measured and are shown in FIG. 3B. As can be seen, dasatinib significantly reduced apoptosis of cells.

Figure 3C:
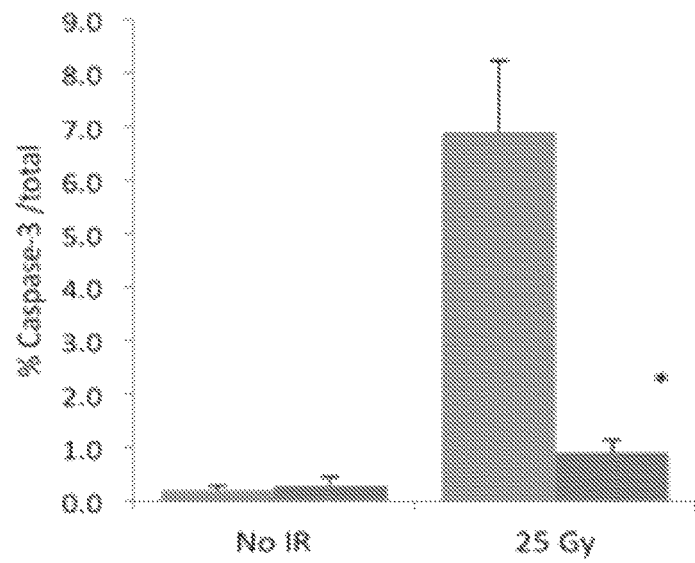
FIG. 3C shows results of suppression of apoptosis in the irradiated salivary gland in mice treated with dasatinib.

Mice were treated with DMSO or 20 mg/kg of dasatinib in DMSO 1 hr prior and 3 hr post irradiation (25 Gy) by oral gavage. The mice were sacrificed 24 hrs later. Parotid gland tissue was stained with anti-act caspase 3 and cells with active caspase-3 were quantified. Average of three mice (>1000 cells per mouse) are shown in FIG. 3C. In FIG. 3C, the data is expressed as % positive/total cells ($p<0.01$).

Example 3

Figure 4:
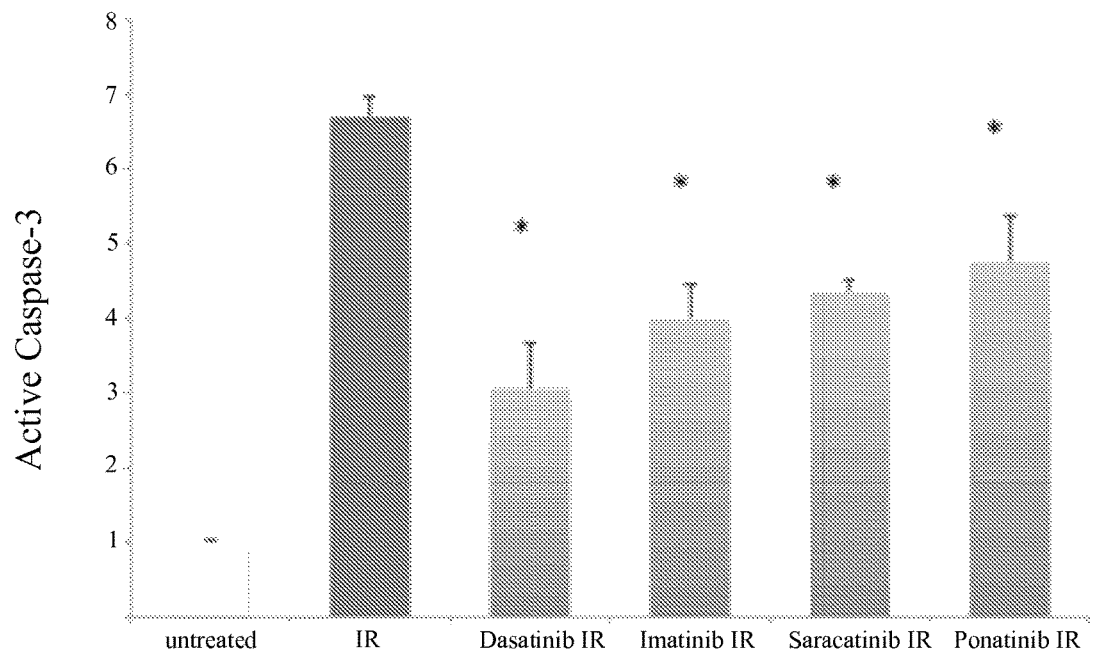
FIG. 4 is a bar graph showing that the TKIs, dasatinib, imatinib, saracatinib and ponatinib, all inhibit irradiation induced apoptosis.

Parotid salivary acinar cells (parC5) were pre-treated with dasatinib, imatinib, saracatinib or ponatinib 30 mins prior to 10 Gy irradiation. Cells were harvested after an additional 18 hrs and casapase 3 activity were measured. As can be seen in FIG. 4 ($p<0.05$), all TKI treated cells showed a significant protection from apoptosis.

Example 4

The efficacy of three tyrosine kinase inhibitors was examined as radio-protectors in the salivary gland in vivo. Briefly, mice were irradiated to the head and neck using a cesium-137 source, with or without administration of dasatinib (20 mg/kg), imatinib (50 mg/kg), or bosutinib (100 mg/kg) by oral gavage 1 hour before and 3 hours after irradiation (see schematic in FIG. 5, panel A, which shows a schematic representation of the experiment outlining times of oral gavage, radiation and saliva collection). The rest of the mouse body was protected by lead shielding. Control mice were gavaged with vehicle alone for dasatinib (80 mM citric acid buffer, pH 2.1) imatinib (water) or bosutinib (0.5% methocel and 0.4% Tween 80). Mouse weight and saliva flow rates were measured prior to irradiation and every 30 days up to 90 days). A minimum of 3 mice were used for each condition in each experiment.

To stimulate salivation, mice were given an intraperitoneal injection of carbachol dissolved in saline (0.25 mg/kg) two minutes prior to measuring salivary flow rate. Saliva was collected for 3 min using a micropipette. Salivary flow rates are expressed as mL/min.

Figure 5:
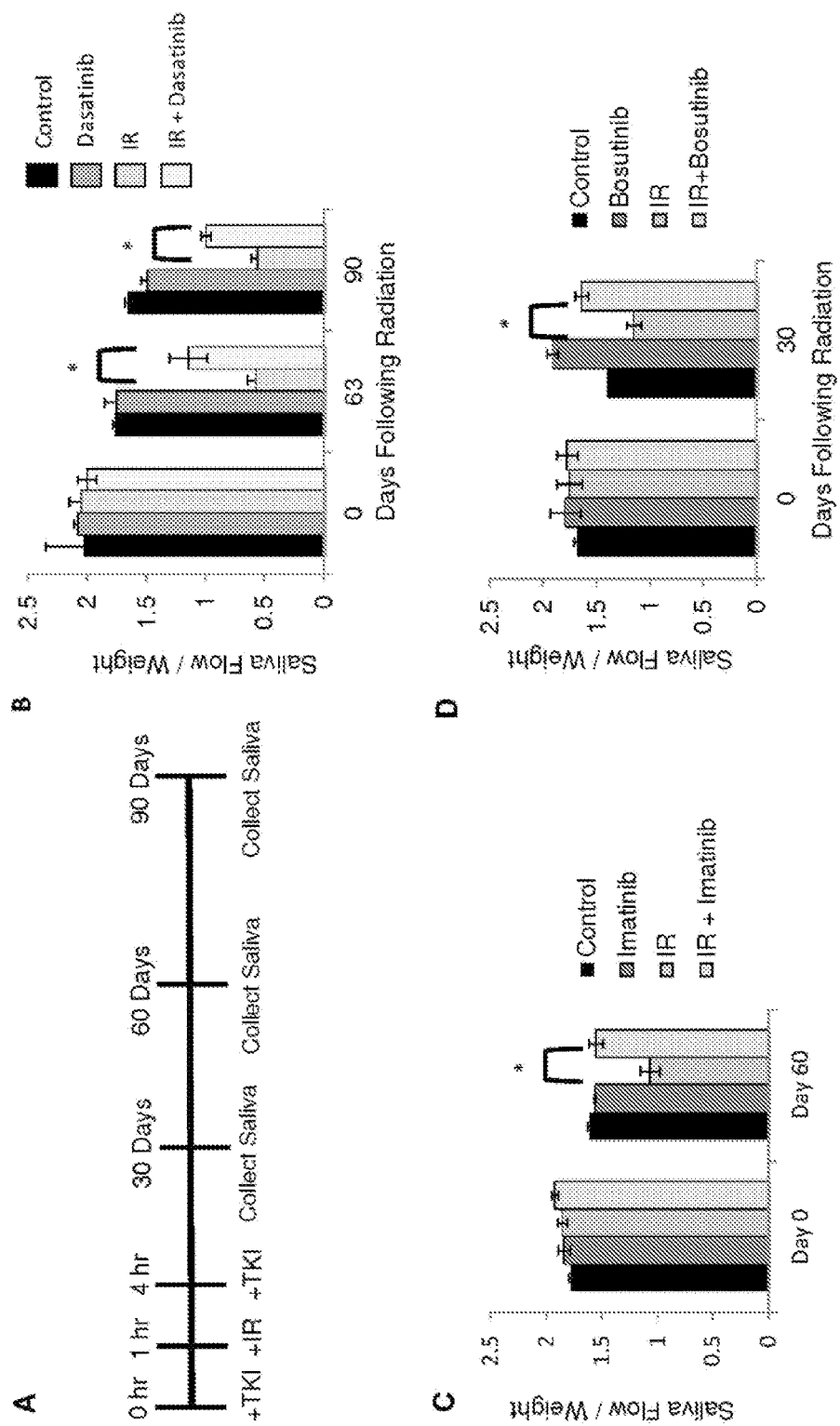
FIG. 5 shows experimental procedure time line (Panel A) and the results of administering Tyrosine Kinase Inhibitor prior to administering radiation to mice (Panels B, C and D).

As shown in FIG. 5 these tyrosine kinase inhibitors preserved salivary gland function following radiation. Panels B and C in FIG. 5 show the results of mice that were irradiated with 10 Gy to the head and neck, with or without the administration of dasatinib (Panel B) and imatinib (Panel C). Panel D in FIG. 5 shows the results of mice that were irradiated with 15 Gy to the head and neck, with or without the administration of bosutinib. A minimum of 3 mice were used for each condition (n=3) and the data represents the average saliva flow rate +/− the standard deviation (asterisk indicates a p value <0.01).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for reducing apoptosis of non-cancerous cells in a cancer patient during a radiotherapy, said method comprising administering a therapeutically effective amount of a tyrosine kinase inhibitor (TKI) that inhibits c-Abl and Src-family kinases to a cancer patient prior to administering a radiotherapy treatment, wherein administration of said TKI reduces the amount of apoptosis of non-cancerous cells compared to receiving said radiotherapy treatment in the absence of said prior administration of said TKI.

2. The method of claim 1, wherein said TKI is selected from the group consisting of dasatinib, imatinib, ponatinib, saracatinib, and a combination thereof.

3. The method of claim 1 further comprising the step of administering a second tyrosine kinase inhibitor to said cancer patient after administering said radiation cancer therapy.

4. The method of claim 1, wherein said cancer comprises head and neck cancer.

5. The method of claim 4, wherein said TKI reduces apoptosis of non-cancerous cells in salivary glands.

6. A method for protecting non-cancerous cells in salivary glands during a radiotherapy in a patient suffering from a head and neck cancer, said method comprising administering a therapeutically effective amount of a tyrosine kinase inhibitor (TKI) that inhibits c-Abl and Src-family kinases to a cancer patient undergoing a radiotherapy cancer treatment, wherein administration of said TKI reduces the amount of apoptosis of non-cancerous cells in salivary glands of said patient compared to receiving the radiotherapy in the absence of administration of said TKI.

7. The method of claim 6, wherein said TKI is administered prior to administration of the radiotherapy.

8. The method of claim 6, wherein said TKI is administered after administration of the radiotherapy.

9. The method of claim 6, wherein TKI is administered before and after administration of the radiotherapy.

* * * * *